(12) United States Patent  (10) Patent No.: US 8,702,922 B2
Asai et al.  (45) Date of Patent: Apr. 22, 2014

(54) CELL MEASURING VESSEL, EXTRACELLULAR POTENTIAL MEASURING METHOD, AND CHEMICAL TESTING METHOD

(75) Inventors: Yasuyuki Asai, Kanagawa (JP); Makoto Nagakura, Tokyo (JP); Takeaki Fukami, Tokyo (JP); Keisuke Oosumi, Tokyo (JP)

(73) Assignee: ReproCELL, Inc., Kanagawa (JP)

( * ) Notice: Subject to any disclaimer, the term of this patent is extended or adjusted under 35 U.S.C. 154(b) by 681 days.

(21) Appl. No.: 12/733,729
(22) PCT Filed: Sep. 17, 2008
(86) PCT No.: PCT/JP2008/066751
§ 371 (c)(1), (2), (4) Date: Aug. 12, 2010
(87) PCT Pub. No.: WO2009/038079
PCT Pub. Date: Mar. 26, 2009

(65) Prior Publication Data
US 2010/0304423 A1 Dec. 2, 2010

(30) Foreign Application Priority Data
Sep. 18, 2007 (JP) ................. 2007-240868

(51) Int. Cl.
G01N 27/26 (2006.01)
G01N 33/50 (2006.01)
C12Q 1/02 (2006.01)
C12M 1/00 (2006.01)
C12M 1/34 (2006.01)

(52) U.S. Cl.
USPC ............ 204/403.01; 435/287.1; 435/29; 422/68.1; 422/82.01; 205/777.5; 204/400; 506/39

(58) Field of Classification Search
USPC ........... 204/400, 403.01, 556, 406; 205/775, 205/777.5; 435/287.1, 29; 422/68.1, 82.01; 424/9.2; 506/10, 39
See application file for complete search history.

(56) References Cited

U.S. PATENT DOCUMENTS

2003/0022387 A1* 1/2003 Oka et al. .................. 436/149
2003/0113833 A1 6/2003 Oka
(Continued)

FOREIGN PATENT DOCUMENTS

EP 1 533 615 5/2005
JP 2-049898 U 4/1990
(Continued)

OTHER PUBLICATIONS

ES cells for drug discovery, Industry News, Medical Science Digest, vol. 33 (14) 2007, pp. 1272-1275, and English translation (4 pages total).
(Continued)

Primary Examiner — Jennifer Dieterle
(74) Attorney, Agent, or Firm — Nash and Titus, LLC

(57) ABSTRACT

The cell observation using a conventional well plate takes much costs. Each well 3 being opened at a top plate 2a of the well plate 1 has a diameter reduced portion 32 which inner circumferential surface 32a is conically hollowed. At a lower portion of the diameter reduced portion 32 is formed an inserting hole 33. In a detecting portion 4, an outer circumferential surface of a round-bar reference electrode 41 is covered by an insulating portion 42. The detecting portion 4 has an upper end portion 4a and a lower end portion 4b which outer circumferential surface is exposed to an outside without being covered by an insulating portion 42. On an upper side above the lower end portion 4b is formed a diameter expanded portion 4c in which an outer circumferential surface of the insulating portion 42 is covered with a measuring electrode 43. The detecting portion 4 is fixed to a well 3 whose diameter expanded portion 4c is inserted into an inserting hole 33 and its upper end portion 4a is contained in the well 3. In the detecting portion 4, the upper end surface 43a of the measuring electrode 43 is communicated with an inner circumferential surface 32a of the diameter reduced portion 32 positioned in an edge surrounding portion of the inserting hole 33.

6 Claims, 13 Drawing Sheets

(56) References Cited

U.S. PATENT DOCUMENTS

| | | | |
|---|---|---|---|
| 2003/0113883 A1* | 6/2003 | Liaw et al. | 435/106 |
| 2005/0279634 A1* | 12/2005 | Ozaki et al. | 204/556 |

FOREIGN PATENT DOCUMENTS

| | | | | |
|---|---|---|---|---|
| JP | 2007-232607 A | | 9/2007 | |
| WO | WO 02/103354 | | 12/2002 | |
| WO | WO 2005/001018 | | 6/2004 | C12M 1/34 |
| WO | WO2005/001018 | * | 1/2005 | |

OTHER PUBLICATIONS

Nakaya, H., "Cell electrical pharmacology evaluation method", J. Pharmacological Sciences and the Pharmaceutical Society of Japan, 2003, vol. 121, pp. 384-392.

English Abstract for Nakaya. H, "Cell electrical pharmacology evaluation method", J. Pharmacological Sciences and the Pharmaceutical Society of Japan, 2003, vol. 121, pp. 384-392.

Bioresearch Center, "Multi-Electrode Array System, MEA60", retrieved online on Sep. 10, 2008 <URL:http://www.brck.co.jp/MCS/meacataloguejp1.pdf>.

English translation of Bioresearch Center, "Multi-Electrode Array System, MEA60", retrieved online on Sep. 10, 2008 <URL:http://www.brck.co.jp/MCS/meacataloguejp1.pdf>.

* cited by examiner

FIG. 5
(a)
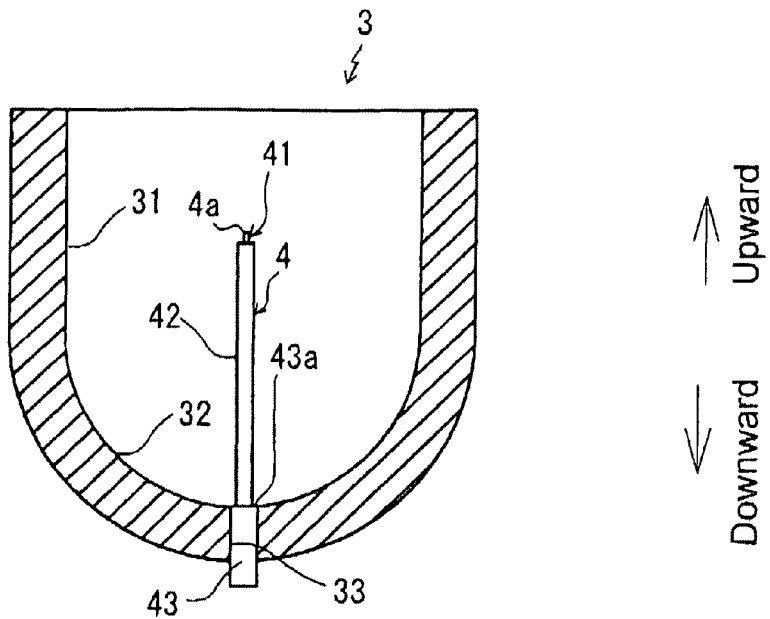
(b)
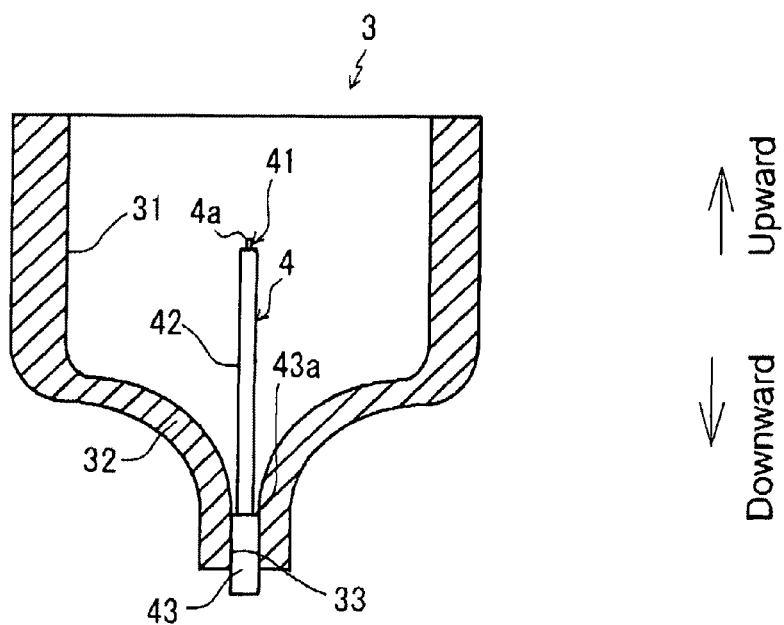

FIG. 6
(c)
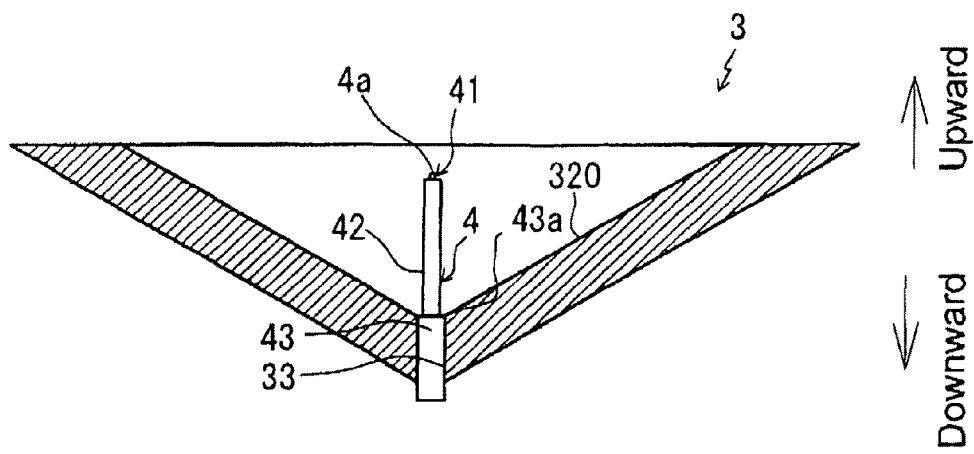
(d)
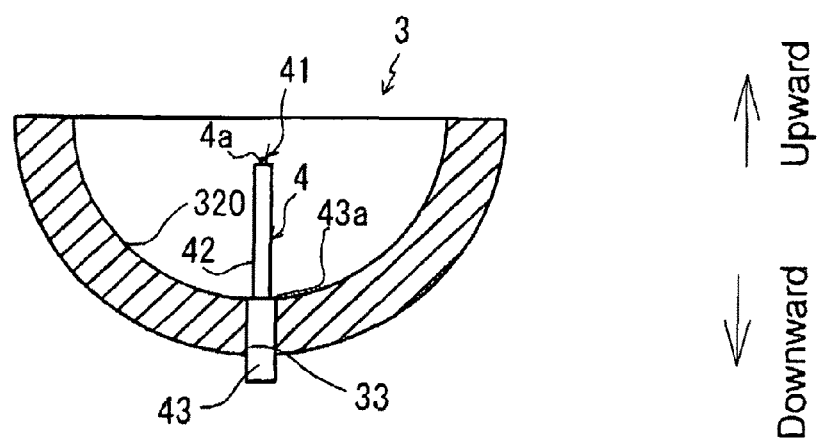

FIG. 7
(e)
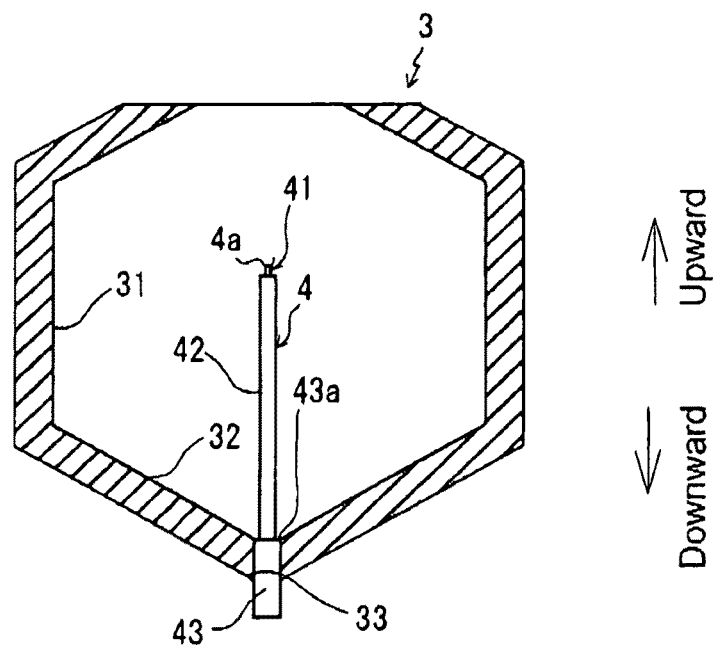
(f)
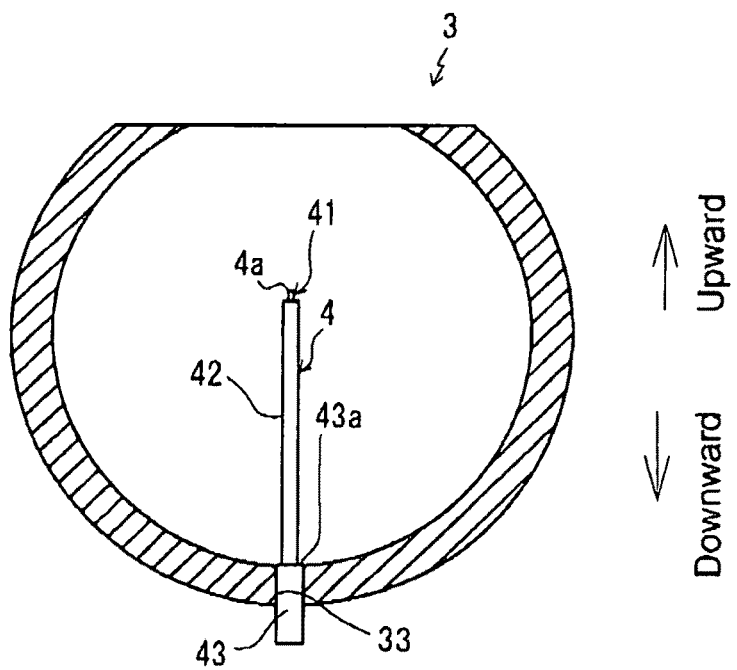

(g)

FIG. 9
(a)
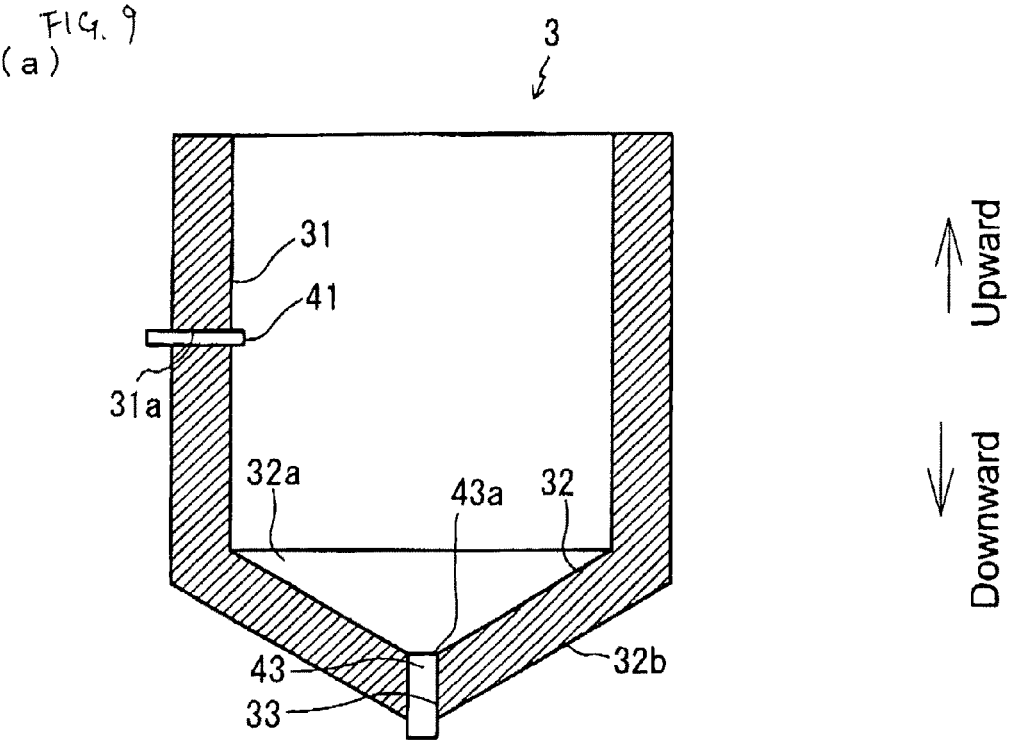
(b)
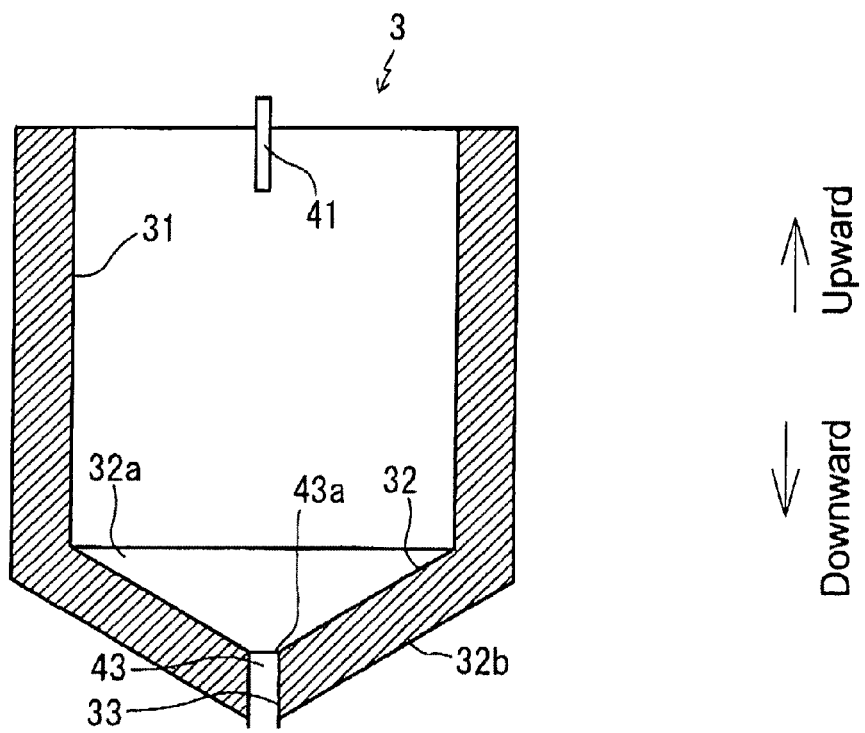

(a) Fig. 10
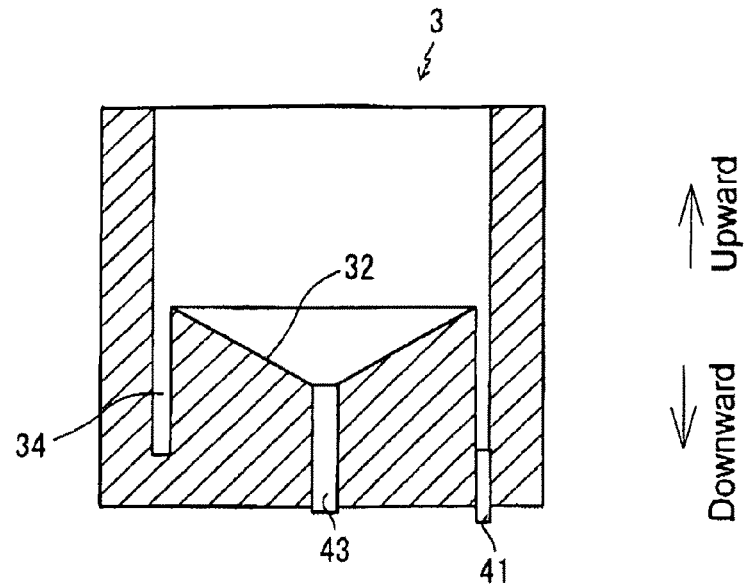
(b)
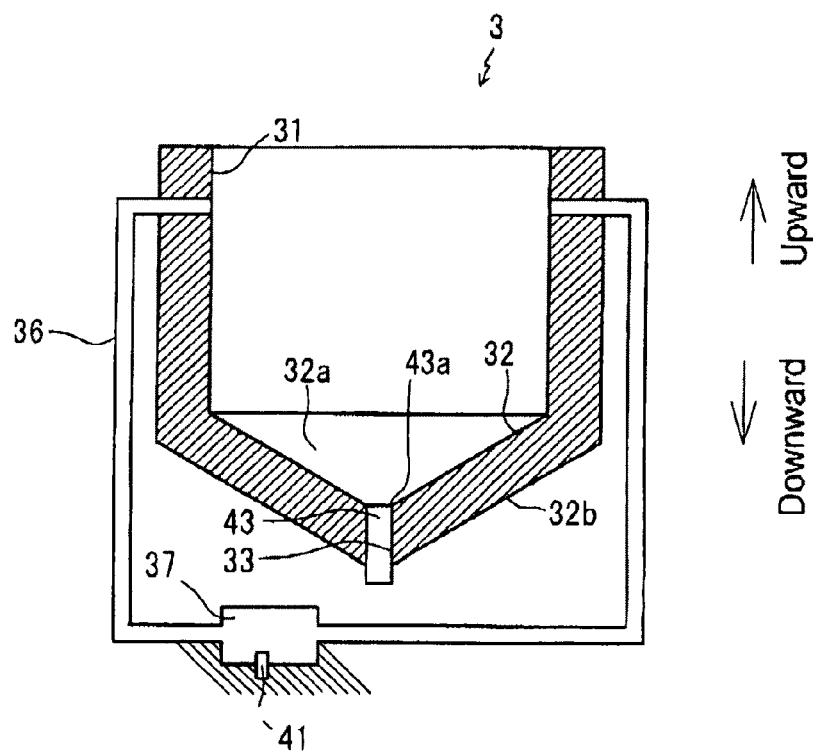

FIG. 11
(a)
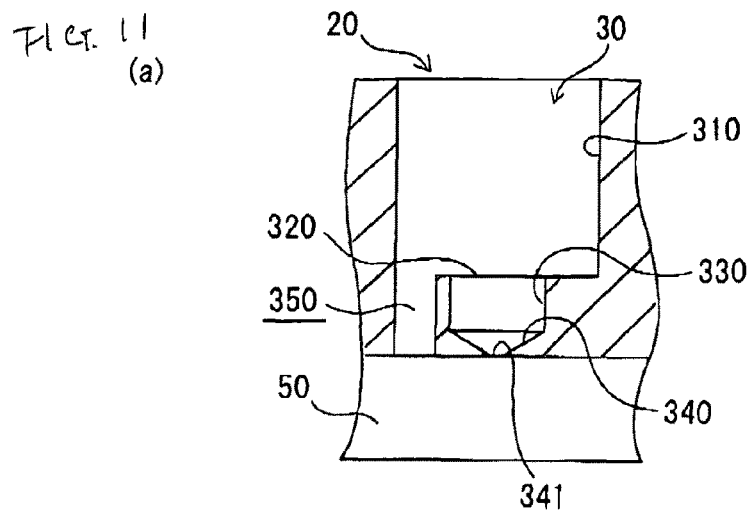
(b)
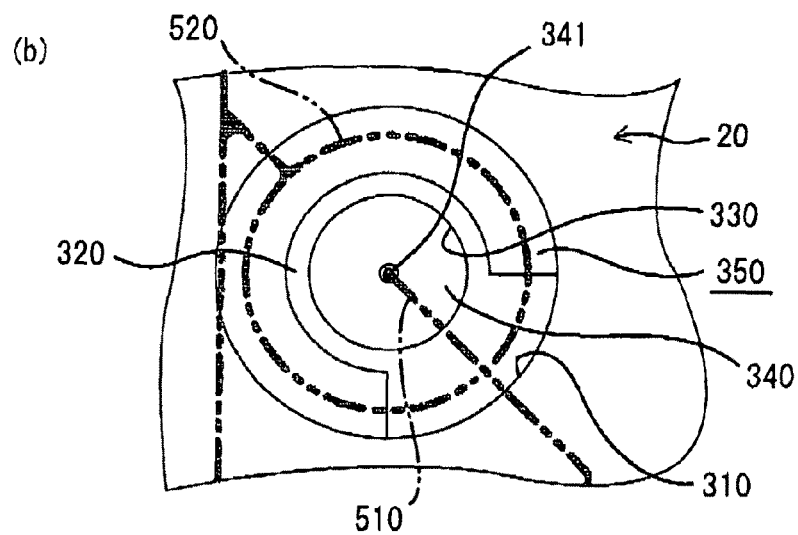
(c)
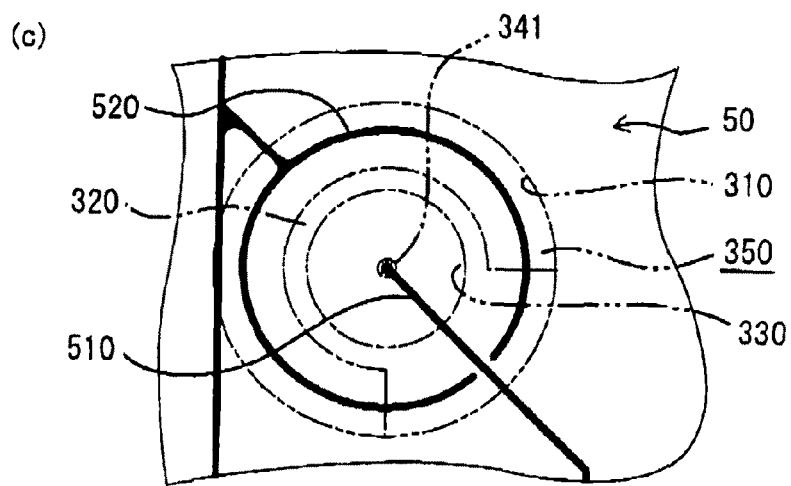

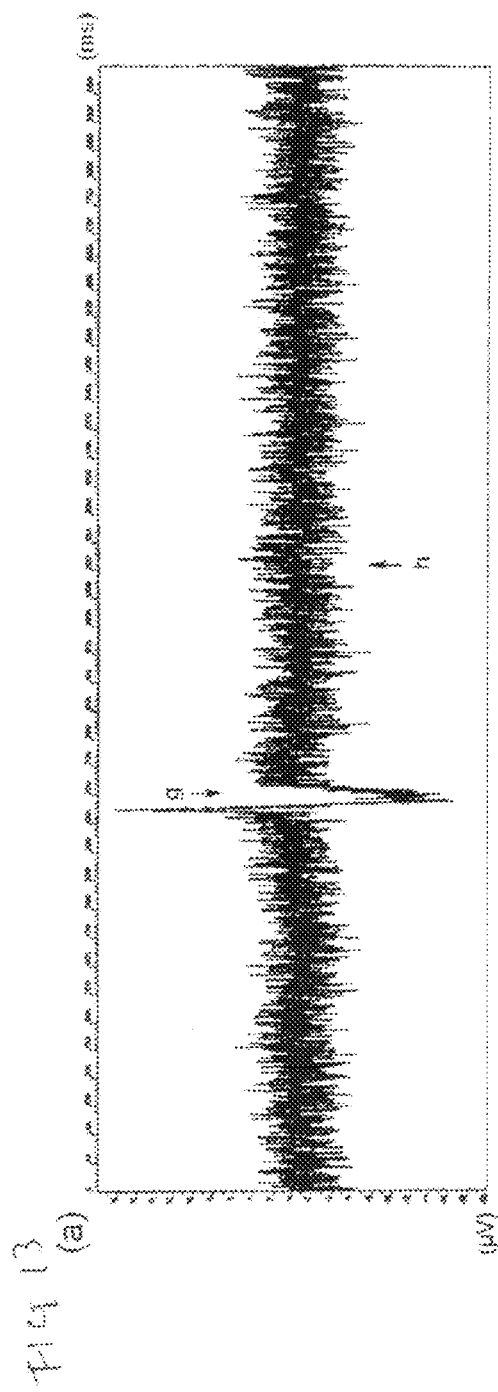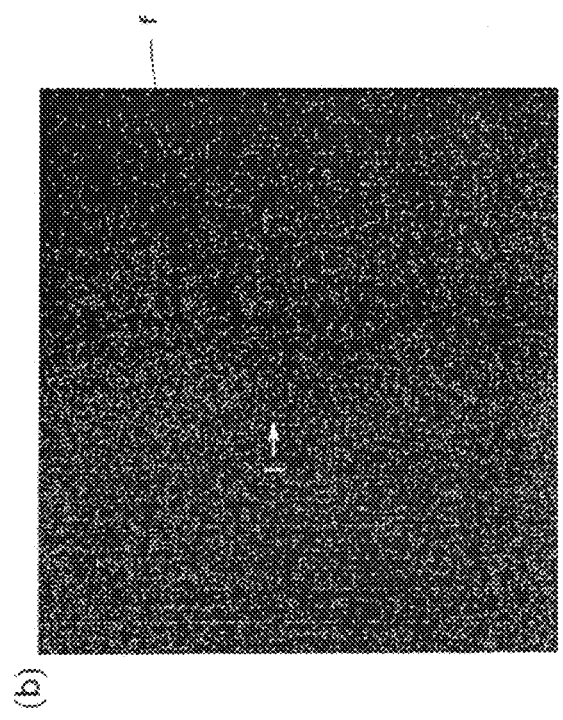
FIG. 13

CELL MEASURING VESSEL, EXTRACELLULAR POTENTIAL MEASURING METHOD, AND CHEMICAL TESTING METHOD

This application claims priority from Japanese application 2007-0240868 (filed Sep. 18, 2007), and PCT International application PCT/JP2008/066751 (filed Sep. 17, 2008). The contents of both applications are incorporated herein in their entirety.

TECHNICAL FIELD

The present invention relates to a cell measuring container having a housing chamber to contain a culture medium and a cell.

BACKGROUND TECHNOLOGY

In a modern development of a new medicine, it is necessary to early ascertain toxicity caused by a drug. As one of the toxicities, drug induced (acquired) long QT syndrome, which is a disease causing serious arrhythmia for a patient is known.

The drug induced QT syndrome is a serious disease in which a QT interval is extended in an electrocardiogram after the administration of a drug, causing TdP (Torsades de pointes, Torsades de pointes is a nonsustained polymorphic ventricular tachycardia) and some occurrence of ventricular fibrillation leading to syncope or sudden death. Actually, out of 25 items of drugs which sales were discontinued in the market of the United States since 1980, 5 items of the drugs were confirmed as doubtful that the drugs might provoke the drug induced QT syndrome.

In this manner, many drugs, which are developed as new drug candidates, drop out at clinical or preclinical stages due to the revealing of their toxicity, and that is a big problem. Therefore, in order to ascertain the toxicity caused by a drug, various test to measure membrane potential have been made by penetrating a cell membrane to insert an electrode into a cell. In this kind of drug test, inspecting the toxicity of the drug at an early stage is required.

As a method for obtaining the test result earlier, an influence of an activity of an ion channel by a drug is observed by a change of a cellular potential of the cell in a culture medium, which the drug is added. In the following non-patent reference 1, a well plate to be used for the test method is disclosed.

The well plate is provided with a plurality of wells, which is opened at an upper face, and each well is for congaing cells with culture medium. At a bottom of each well is formed in a flat manner and is disposed a measuring electrode and a grounded reference electrode.

When a cell is in touch with the measuring electrode in the well, extracellular potential of cells changing by an activity of an ion channel is applied to the measuring electrode, and it causes a potential difference between the measuring electrode and reference electrode. By measuring a change in the potential difference between the both electrodes before and after the adding of the drug, an influence of a drug to a cell is observed.

Non-patent reference 1: Bioresearch Center Co., "QT screen", [online], [Aug. 27, 2007], Internet <URL: http//www.brck.co.JP/MCS/qtscreencataloguejpl.pdf>

SUMMARY OF THE INVENTION

Problems to be Solved by the Invention

In the observation by using the above conventional well plate, it was necessary to make cells contacted with a measuring electrode. However, the conventional well plate was flat. Thus, even if a cell was applied, since it was impossible to surely determine a position where cells at a bottom to be adhered, attaching the cells to a fine measuring electrode disposed at the flat bottom of the well is very hard. As result, a large number of cells, such as 10 million cells per well, were required to be supplied to each well. Therefore, inspection cost was expensive because many cells needed to be used. In the ES cell-derived cardiac muscle cells, a sufficient number of the cells could not be provided, so performing the test was actually impossible.

The present invention has been made in light of the problems described above and has as an objective to solve the above problems.

Means for Solving Problems

According to a first aspect of the present invention, there is provided a cell measuring container including housing chambers each being opened at its upper face and housing a cell together with a culture medium, wherein the housing chamber has a diameter reduced portion whose diameter of an inner circumferential surface is reduced from an upper end side toward a lower end side and has a measuring electrode placed in the lower end side of the diameter reduced portion.

According to a second aspect of the present invention, there is provided a cell measuring container, further including a reference electrode placed in a position apart from the measuring electrode so as to avoid contact with a cell.

According to a third aspect of the present invention, there is provided a cell measuring container, wherein the measuring electrode covers a partial circumferential surface or entire circumferential surface in a circumferential direction of the reference electrode with an insulating portion being interposed between the measuring electrode and reference electrode, wherein the reference electrode is formed so that an upper end side above a portion whose outer circumferential surface is covered by the measuring electrode is exposed to an outside from the insulating portion and so as to face an inside portion of the housing chamber.

According to a fourth aspect of the present invention, there is provided a cell measuring container including a housing chamber being opened at its upper face, a detecting section having a measuring electrode and a reference electrode extending from a lower end portion of the housing chamber toward an upper end portion of the housing chamber, wherein the housing chamber has a diameter reduced portion whose diameter of an inner circumferential surface is reduced from an upper end side toward a lower end side and a through hole passing through a lower end portion of the diameter reduced portion in upward and downward directions and wherein the detecting section is formed so as to cover, with an insulating portion, an outer circumferential surface of a bar-like reference electrode, except an upper end portion and lower end portion, and so as to cover an outer circumferential surface of a lower portion of the insulating portion with the measuring electrode, and wherein an upper end side of the measuring electrode inserted fluid-tight into the inserting hole faces the inside portion of the housing chamber and a lower end side protrudes in a lower end portion of the housing chamber and an upper end portion of the reference electrode is positioned in the housing chamber.

According to a fifth aspect of the present invention, there is provided a cell measuring container including a through hole formed at a position opposite to the inserting hole formed in the housing chamber, the reference electrode positioned in an edge portion surrounding the through hole and having a pair of connecting portions formed on upper and lower faces of the reference electrode connected to each of the connecting portions, and a wiring substrate to connect the measuring electrode to external devices, wherein a lower end portion of the reference electrode having passed through the through hole is connected to the connecting portion in the lower face and a lower end portion of the measuring electrode inserted into the through hole is connected to the connecting portion of the upper face.

According to a sixth aspect of the present invention, there is provided a cell measuring container, wherein the measuring electrode and the reference electrode are formed on the wiring substrate having the housing chamber and wherein the diameter reduced portion causes the measuring electrode to face an opening on the lower end and wherein, in an internal face of the housing chamber is opened an upper end opening of the through hole extending apart from the diameter reduced portion and the lower end is faced by the reference electrode.

According to a seventh aspect of the present invention, there is provided a cell measuring container including a housing chamber being opened at its upper face, and a wiring substrate having a measuring electrode, a reference electrode, and the housing chamber, wherein the housing chamber has a large diameter portion extending downward from an upper end opening and a small diameter portion extending downward from the large diameter portion through a step difference, wherein the small diameter portion has a diameter reduced portion whose diameter of an inner face is reduced from an upper end side to a lower end side and whose lower end opening is faced by the measuring electrode, and wherein on an upper face of the step difference portion is mounted an upper opening of a through hole extending apart from the small diameter portion and the lower end opening of the through hole is faced by the reference electrode.

According to an eighth aspect of the present invention, there is provided an extracellular potential measuring method for measuring the extracellular potential of a cell using the cell measuring container described herein, including a process of supplying a culture medium to the containing chamber until an inner circumferential surface of the diameter reduced portion is covered by the surface of the culture medium, a process of supplying a cell by introducing the cell to be measured into a culture medium supplied in the culture medium supplying process, a process of additionally supplying a culture medium to the housing chamber until the reference electrode is soaked at times before the cell introduction in the cell supplying process, or after the cell introduction, or after the adhesion of the introduced cell to the measuring electrode, and a process of measuring an extracellular potential of a cell contained in the housing chamber based on a potential difference between the reference electrode soaked in a culture medium in the process of additionally supplying a culture medium and the measuring electrode.

According to a ninth aspect of the present invention, there is provided a drug testing method using the extracellular potential measuring method for measuring the extracellular potential of a cell described above, wherein an extracellular potential is measured by the process of measuring an extracellular potential before and after the supply of a drug to be inspected into the housing chamber to inspect an influence of the drug to be inspected on activity of a cell.

The effect of the invention is to enable and provide a well plate that can reduce the cost for a cell to the test.

BRIEF DESCRIPTION OF DRAWINGS

FIG. 1(a) is a plan view, FIG. 1(b) is a front view, and FIG. 1(c) is a side view.

FIG. 5 is a first diagram explaining a modified example of a well mounted in a well plate.

FIG. 6 is a second diagram explaining a modified example of a well mounted in the well plate.

FIG. 7 is a third diagram explaining a modified example of a well mounted in the well plate.

FIG. 9 is a fifth diagram explaining a modified example of a well mounted in the well plate.

FIG. 10 is a sixth diagram explaining a modified example of a well mounted in the well plate.

FIG. 11 is a seventh diagram explaining a modified example of a well mounted in the well plate.

FIG. 12(a) is a measurement diagram showing a state where a pulsation cell exists (multi-electrode single dish), FIG. 12(b) is a measurement diagram showing a state where no pulsation cell exists (cell measurement container of the embodiment of the present invention), FIG. 12(c) is a measurement diagram showing a state where a pulsation cell exists (cell measurement container of the embodiment of the present invention), and FIG. 12 (d) shows a microscopic photo showing a position of a pulsation cell and a measuring electrode.

FIG. 13 is a photograph showing a measurement example of extracellular potential of a cell and FIG. 13(a) is a measurement diagram showing a state where a pulsation cell is adhered to a measuring electrode, and FIG. 13 (b) shows a microscopic photograph showing a position of a pulsation cell and a measuring electrode.

BEST MODE CARRYING OUT THE INVENTION

Figure 1:
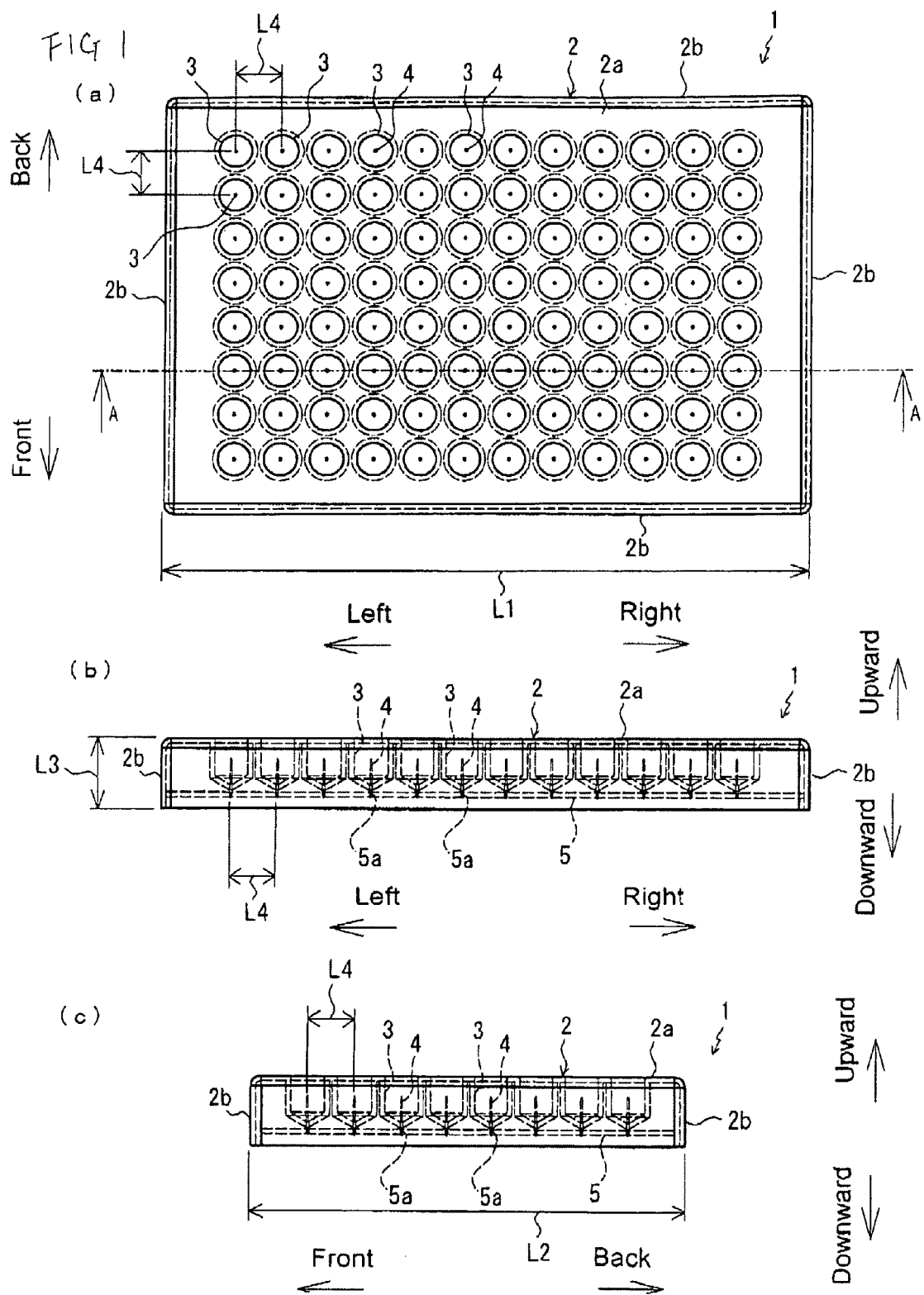
FIG. 1 is a view showing a well plate of the first embodiment of the present invention.

Hereinafter, by referring to drawings, the best mode of the present invention is described. FIG. 1 shows a diagram showing a well plate 1 of the present embodiment. FIG. 1(a) is a plan view, FIG. 1(b) is a front view, and FIG. 1(c) is a side view. In addition, each direction of back and front directions, right and left directions, and up and down directions used in the descriptions is shown in each of drawings.

The well plate 1, as shown in FIG. 1, is a 96-well type plate, which has, in plate main body 2, 96 pieces of wells 3 each serving as a containing chamber to contain a cell and a culture medium. The plate main body 2 includes a top plate 2a having an approximately rectangular plane portion, a side plate portion 2b extending downward from four side portions, which are front and back, left and right, upward and downward, and has a rectangular box shape, and a lid-like shape as a whole.

On an upper surface of the plate main body 2, an upper end opening of each well 3 having a circular opening shape is formed respectively. In back and front directions, eight pieces of wells 3 are arranged. In right and left directions, twelve pieces of wells 3 are arranged. Each of them is arranged at an equal interval and in a rectangular arrangement, and all of the wells 3 are opened at upper surfaces of the top plate 2a. The plate main body 2 having such configurations as above is made up of a resin having electrical insulating properties such as polystyrene or the like, which is also suitable to a cell culture.

In the present embodiment, the outer dimension of the plate main body 2 is 1-2004 to 4-2001 in accordance with ANSI (American National Standards Institute)/SBS (Society for biomolecular science) specifications. More specifically, a length L1 of the right and left directions is set to be 127.8 mm, a length L2 of the front and back directions is set to be 85.5 mm and, a height L3 of the up and down directions is set to be 14.5 mm. Moreover, an arrangement interval L4 (interval between the centers) of each well in the front and back directions and the right and left directions L4 is set to be 9 mm.

Figure 2:
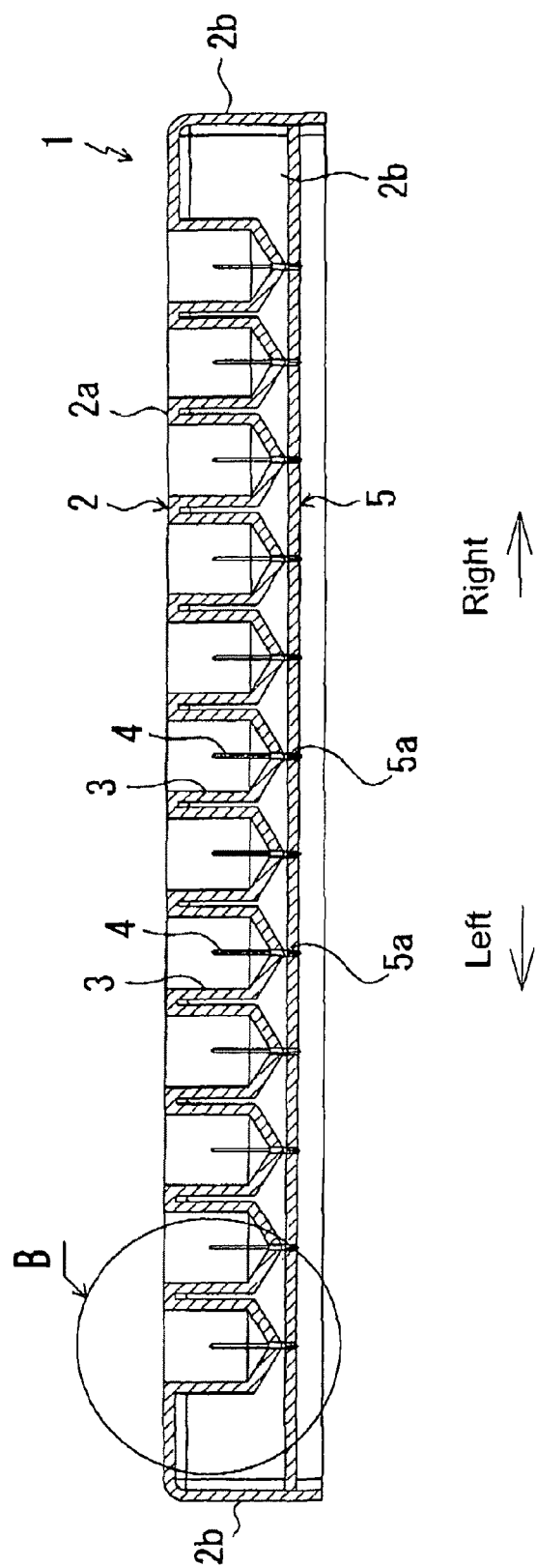
FIG. 2 is a diagram explaining a cross-sectional structure of a well plate and is a perspective view as a cross section of A-A line shown in FIG. 1.
Figure 3:
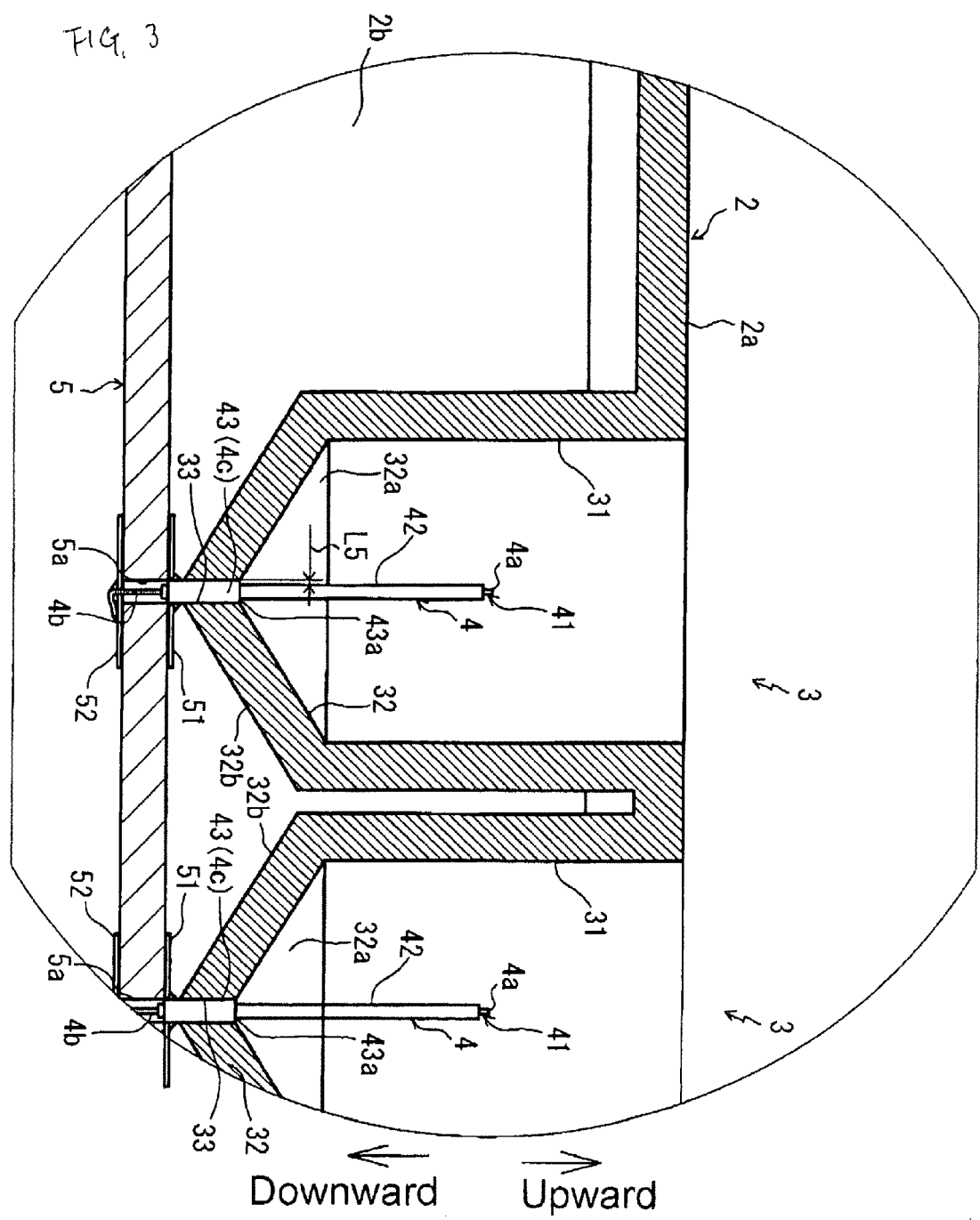
FIG. 3 is a cross-sectional view showing a well and wiring substrate and also a diagram showing a partially expanded portion indicated by an arrow B in FIG. 2.

FIG. 2 is a diagram explaining a cross-sectional structure of the well plate 1 and is a cross-sectional view of the well plate 1 taken along the line A-A in FIG. 1(a). FIG. 3 is a cross-sectional view of the well 3 and wiring substrate 5 and also a diagram showing a partially expanded portion indicated by an arrow B of FIG. 2.

As shown in FIG. 2, each of the wells 3 is comprised integrally with the top plate section 2a and is made up of a detecting section 4 having the same configuration, respectively. In the lower end portion of the plate main body 2 is provided the wiring substrate 5 having a rectangular plane being approximately the same in size as the top plate 2a.

The wiring substrate 5 is attached to the plate main body 2 in a fixed manner being attached to an inner face of the side plate 2b of the plate main body 2. In each well 3, a through hole 5a through which the detecting section 4 is inserted is formed in the wiring substrate 5. Each through hole 5a is formed in the wiring substrate 5 in the same manner as in other wells 3 formed in the top plate 2a of the plate main body 2.

As shown in FIG. 3, the well 3 has a cylindrical portion 31 extending downward vertically from the top plate 2a and a diameter reduced portion 32 extending downward from a lower edge portion of the cylindrical portion 31. The diameter of the diameter reduced portion 32 is reduced along its upper side to its lower side and has a conically hollowed inner surface 32a. In the well 3, an inserting hole 33 that passes through an lower end of the diameter reduced portion 32 from an inner circumferential surface 32a to an outer circumferential surface 32b is formed. The inserting hole 33 is a hole, which the inspecting section 4 passes, and has a circular opening shape. The inserting hole 33 is opened in a central portion of the inner circumferential surface 32a of the diameter reduced portion 32 having a circular plane shape.

The detecting section 4 to be inserted into the inserting hole 33, as shown in FIG. 3, is formed that an outer circumferential surface of the reference electrode 41 is covered by an insulating portion 42. The reference electrode 41 is shaped as an electrode bar having a circular bar like and made of metal, such as gold, platinum, stainless, or the like. The insulating portion 42 is configured by coating the reference electrode 41 with a resin having electrical insulation property, such as polystyrene.

The detecting section 4 has an upper portion 4a and a lower end portion 4b which are exposed to the outside, where the outer circumferential surface of the reference electrode 41 is not covered with the insulating portion 42. The detecting section 4 is provided with a diameter expanded portion 4c which is formed in an upper direction of the lower end portion 4b and its diameter is expanded so as to be made almost equal to the inserting hole 33 by covering the outer circumferential surface of the insulating portion 42 with a measuring electrode 43. The measuring electrode 43 is configured by coating the insulating portion 42 with metal such as gold, platinum, or stainless steel. The upper end surface 43a of the measuring electrode 43 is so constructed as to be flat and has a width L5 which is wide enough to put a cell to be measured. The width L5 can be set to be any length in a range of about 1 μm to 3 mm depending on kinds of plates such as 384-well type or 1536-well type plate besides 96-well type plate. Moreover, cells to be measured are placed on the upper end surface 43a, and, therefore, the thickness L5 of the measuring electrode 43 is allowed to be set depending on cells to be measured.

In the detecting section 4 having such a configuration, the diameter expanded portion 4c inserted in the inserting hole 33 is fixed to an inner surface of the inserting hole 33. In the detecting section 4 fixed in the well 3, the upper end portion 4a placed in an upper direction of the inserting hole 33 is contained in the well 3, and the lower end portion 4b placed in an lower direction of the inserting hole 33 is inserted into the through hole 5a of the wiring substrate 5. Also, in the detecting section 4, the upper end surface 43a of the measuring electrode 43 is allowed to lie along the inner circumferential surface 32a of the diameter reduced portion 32 positioned in a surrounding edge of the inserting hole 33. The upper end portion 4a of the detecting section 4 made up of the reference electrode 41 is positioned, by providing a distance, between the upper end portion 4a and the measuring electrode 43 enough to diffuse ions, which is moved from a cell placed on the upper end surface 43a of the measuring electrode 43 to outside of the cell membrane, to its outside in the culture medium, in an upper direction from the upper end portion of the diameter reduced portion 32.

As shown in FIG. 3, the through hole 5a formed on the wiring substrate 5 passes through between an upper face and a lower face of the wiring substrate 5 and has a circular opening shape which is the same in diameter as the inserting hole 33. In the surrounding edge portion of the through hole 5a, an upper face connecting wiring 51 covering an upper face of the wiring substrate 5, and a lower face connecting wiring 52 covering a lower face of the wiring substrate 5 are formed. The upper face connecting wiring 51 and lower face connecting wiring 52 are formed in a manner similar to the method in which a pattern is formed by etching on a normal printed circuit board, and that is a gold-plated copper wiring in its surface.

In the upper face connecting wiring 51, its inner circumferential surface lies along the inner circumferential surface of the through hole 5a and has a circular shape being approximately equal in diameter to that of the through hole 5a. In the lower face connecting wiring 52, the inner circumferential edge portion protruded to inside to through hole 5a has a circular shape, which is larger in diameter than the reference electrode 41. The upper face connecting wiring 51 and lower face connecting wiring 52 are connected, via wiring (not shown) of the wiring substrate 5, to the external device.

In the upper face connecting wiring 51, into an opening making up the inner circumferential surface of the through hole 5a lain along its inner circumferential surface is inserted a lower end portion of the diameter expanded portion 4c protruded from the lower end opening of the inserting hole 33 formed in the well 3 and is then electrically and mechanically connected with the measuring electrode 43 covering an outer circumferential surface of the insulating section 42 at the diameter expanded portion 4c. In the lower face connecting wiring 52, into the opening, which the inner circumferential surface, is placed in an inner portion of the through hole 5a is inserted the lower end portion 4b and is then electrically and mechanically connected at the lower end portion 4b of the detecting section 4 having passed through the through hole 5a formed in the wiring substrate 5 to the reference electrode 41, which the outer circumferential surface is exposed.

Figure 4:
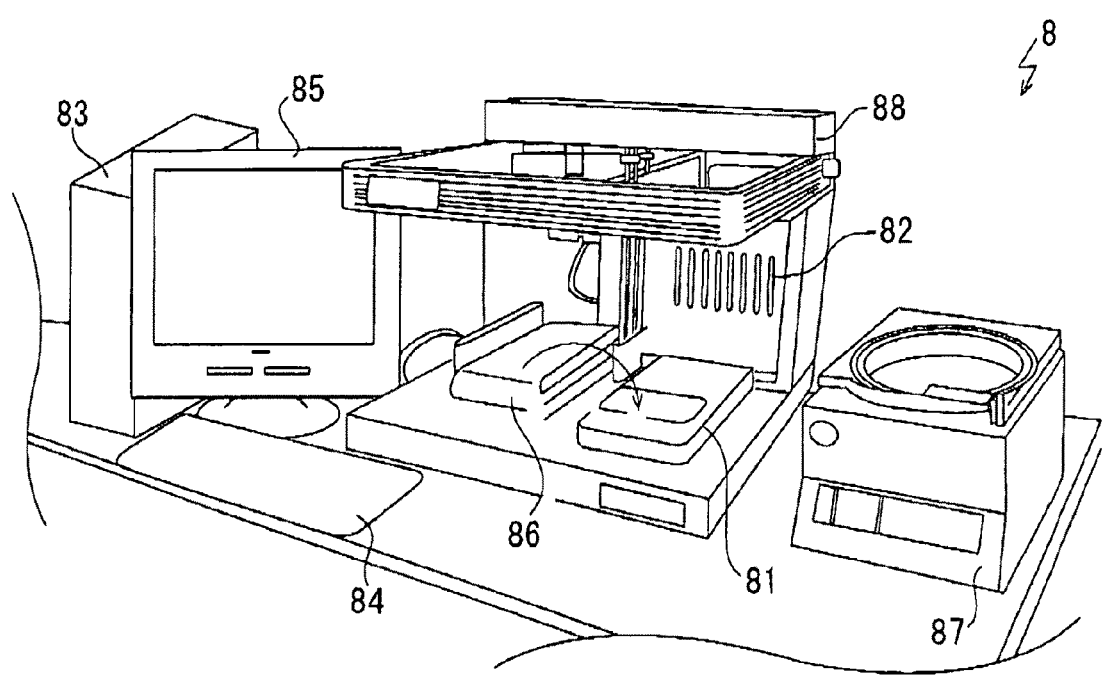
FIG. 4 is an appearance diagram in outline and shows a configuration of a drug testing apparatus to make a drug test based on the measurement of extracellular potential by using a well plate as shown in FIG. 1.

Then, as one example of performing observation of a cell by using a well plate 1, drug testing method based on an extracellular potential (membrane potential) measurement is explained. FIG. 4 is an appearance diagram showing diagrammatically configurations of a drug testing apparatus 8 to be used for the drug test method.

The drug testing apparatus 8 is configured to measure an extracellular potential of a cell by using a well plate. By comparing the result from the measurement of an extracellular potential before and after supplying an testing drug to cells, inspects an influence of an testing drug on an activity of a cell. As shown in FIG. 4, the drug testing apparatus 8 comprises a stage 81 on which a well plate is placed, a drug supplying device 82 to supply a drug to each well providing in a well plate, a measuring device 83 to measure and analyze an extracellular potential of a cell in each well. Also, the drug testing apparatus 8 includes an environmental adjusting device 86 to perform environmental adjustment of $CO_2$ concentration, temperature or the like, in each well having in the well plate, a centrifugal machine 87 to apply centrifugal force to a well plate, and a transporting device 88 to transport a well plate between the stage 81 and centrifugal machine 87. In the measuring device 83, an input device 84 for inputting of information, a display device 85 to display analyzed results, etc., on a display screen is connected. In accordance with input information from the input device 84, measures and analyzes an extracellular potential and controls each portion such as a drug supplying device 82.

When an observation of cells by using a well plate 1 by the drug testing apparatus 8 is to be performed, a cell to be inspected is applied one by one from an upper end opening into each well 3 of the well plate 1 placed on the stage 81 by a micro pipette, or a device by using cell sorter, flow cytometry, etc. As the cell to be tested, a cell having a diameter about 5 μm to 20 μm, including a nerve cell, hepatic cell, cardiac muscle cell, and other any cell, can be used. Also, the above cell (s) can be used singly or plurally. As a plurality of cells, a cell mass may be used. The cell is applied in a state in which the upper end portion 4a of the detecting portion 4 is placed above a liquid surface and a culture medium is supplied into the well 3 until the entire inner circumferential surface 32a of the diameter reduced portion 32 is covered by the liquid surface. This enables the prevention of cells supplied in a culture medium from adhesion to the reference electrode 41. Moreover, cells may be applied in any position of the well 3 placed in an upward direction of the diameter reduced portion 32. Therefore, work for applying cells can be simplified. However, in order to avoid the contact between the micropipette or the like and the detecting section 4 or in order to avoid the adhesion of cells to the reference electrode 41 which outer circumferential surface is exposed at the upper end portion 4a of the detecting section 4, the work of cell application is preferably performed in a culture medium placed apart from the detecting section 4.

The cell applied into the culture medium is precipitated by self weight in the culture medium toward the inner circumferential surface 32a of the diameter reduced portion 32 and then moves in the inner circumferential surface 32a of the diameter reduced portion 32 being descent slanted along the central portion where the inserting hole 33 is opened from the circumferential edge portion lain along the cylindrical portion 31 as it is. Thus, after the cell to be tested is applied into the well 3, the well plate 1 on the stage 81 is transported to the centrifugal machine 87 by the transporting machine 88, and centrifugal force is then applied by the centrifugal machine 87 to the lower direction of the well plate 1. The cell moves to the upper end surface 43a of the measuring electrode 43 lain along the inner circumferential surface 32a of the diameter reduced portion 32, puts the detecting section 4 to be stopped, and stays on the upper end surface 43a of the measuring electrode 43.

Thereafter, the well plate 1 is returned back by the transporting machine 88 from the position of the centrifugal machine 87 to the position of the stage 81, and the environmental adjusting device 86 is rotated to the direction shown by an arrow, and the well plate 1 is covered by the environmental adjusting device 86. Then, while the environmental adjusting device 86 is adjusting an environmental state of culture media of each well 3, the adhesion of the cell to the upper end surface 43a of the measuring electrode 43 is waited for. After confirming that the cell is adhered to the upper end surface 43a, the environmental adjusting device 86 is rotated in a direction reverse to the direction shown in the arrow to expose the well plate 1, and the culture medium is additionally poured into the well 3 until the reference electrode 41, which outer circumferential surface is exposed on upper end portion 4a of detecting section 4, is soaked in the culture medium. Here, the adhesion means the state where a structure as like focal adhesion is made in the cell on the upper end surface 43a of the measuring electrode 43 as in the case of the culture plate, and the cell is fixed on the upper end surface 43a. After such operations as above are performed on each well for every work of applying of cells and additional pouring of the culture medium, the measurement of extracellular potential of the cell is carried out.

The observation by the measurement of the extracellular potential of a cell is performed by measuring the potential of the measuring electrode 43 by using the measuring device 83 with a potential of the reference electrode 41 employed as a reference potential. That is, due to the application of the extracellular potential of a cell being adhered to the measuring electrode 43, a potential difference occurs between the measuring electrode 43 and reference electrode 41. By measuring the potential difference by using the measuring device 83 and by analyzing the measured result, the extracellular potential of a cell is performed. Then, in the state where the extracellular potential of a cell measurement is to be carried out, a drug to be tested is supplied by the drug supplying device 82 to the well 3 in which a cell to be measured is contained. The concentration of the drug may be arbitrary, and the drug may be dissolved in a proper solvent such as DMSO (Dimethyl Sulfoxide,) or the like, or the drug may be dissolved directly in a measuring liquid such as culture media for measurement. At the time of the measurement, the extracellular liquid may be replaced with an appropriate culture media for measurement or a buffer solution for measurement. At this time, if necessary, the drug can be diffused in the culture medium by vibrating the stage 81 after having supplied the drug. After the adhesion of a cell, by performing the operations described above, repelling the cell from the upper end surface 43a of the measuring electrode 43 caused by the vibration or the like can be prevented. The supply of a medicine changes a measuring value of an extracellular potential. Thus, by evaluating the influence of the drug on the cell based on a state of the change of the measuring value after and before the supply of the drug, the medicine is inspected by the drug testing apparatus 8.

For example, when a pulsating cardiac cell is used as a cell to be measured, an extracellular potential of a cardiac muscle cell changing due to a pulsating operation is applied to the measuring electrode 43, and a difference in potential with the reference electrode 41 changes accordingly. When cells such as HEK (Human Embryonic Kidney) cell, CHO (Chinese Hamster Ovary) cell, BHK (Baby Hamster Kidney) cell, or the like, which has forcedly expressed an ion channel such as hERG (human Either-a-gogo Related Gene) channel is to be used as a cell to be measured, extracellular potential occurring due to cellular activities is applied to the measuring electrode 43. Therefore, a potential difference occurs with the reference electrode 41, and extracellular activities changes with an activity of a cell. In the measuring device 83, the changes of these potentials are measured, and analysis is performed based on the measuring result. In the case of measuring an extracellular potential of a cardiac muscle cell, the measuring device 83 detects a sharp peak ($Na^+$ current peak: QRS wave-like waveform) and a peak ($K^+$ current peak: T wave like waveform) indicating a slow rise occurring thereafter, and, therefore, the prolongation of QT interval of electrocardiograph wave caused by a specified drug. It is known that the cause of induction of the drug induced long QT syndrome is that, due to the affect of the drug pulsation of the heart on an ion channel, which is a trans-membrane protein existing on a cell surface and is a protein allowing a specified ion to selectively pass through, the harmonious pulsation of the heart is inhibited and causes the prolongation of the QT internal. (Haruoka Nakaya., "Cell electrical pharmacology evaluation Method", Journal of pharmacological sciences and the Pharmaceutical Society of Japan, 2005, Vol. 121-06, pp. 384-392). By performing these analyses described as above with supplying drugs, various evaluations based on changes of extracellular potential of a cell can be carried out.

As described above, according to the present embodiment, cells put in each well moves by self weight toward the measured electrode 43 on the inner circumferential surface 32a of the diameter reduced portion 32 inclined from the upper end side of the well along the lower end side and become in contact with the upper end surface 43a of the measured electrode 4. Therefore, after being ensured to contact, the cells and the measured electrode 43 can be stabilized. This enables highly accurate test to be performed without using many cells, and, thus, the number of cells for inspection can be decreased. The re-investigation by the test can be avoided, and the inspection time can be shortened. As a result, costs for the test can be reduced.

Also, according to the present invention, by simple work of supplying cells at an arbitrary place in the culture medium, the cells ensured to be in contact with the measuring electrode 43. Thus, the extracellular potential can be measured without being troubled by the working of positioning of supplying cells. As a result, this enables the shortening of test time, and costs for tests can be decreased.

Also, according to the present embodiment, unlike the conventional case, without breaking a cell membrane to insert an electrode into cells, and, based on a potential difference between the measuring electrode 43 having been in contact with the cells put on the measuring electrode 43 and a reference electrode 41, the extracellular potential can be measured. Thus, it enables to measure extracellular potential without being troubled by working of the positioning of the electrode. As a result, the test time can be reduced, and the cost can be decreased for the test.

Also, according to the present embodiment, the extracellular potential of a cell being positioned on the upper end surface 43a of the measuring electrode 43 can be measured, both the measurement of the extracellular potential and the observation by using an electroscope can be simultaneously achieved. As a result, when compared with the case that observation by using the microscope and the measurement of the extracellular potential, independently, the test time can be shortened, and costs for the test can be reduced.

Also, according to the present embodiment, the measurement of extracellular potential is performed, without grounding the reference electrode 41, based on a potential of the measuring electrode 43 as a reference to the potential of the reference electrode 41. In this case, even if an in-phase noise is applied accidentally to the measuring electrode 43 and reference electrode 41, by performing differential amplification of the potential between the reference electrode 41 and the measuring electrode 43, changes in the potential difference between both the electrodes caused by the noise, and the influences by noises on the measured result of the extracellular potential can suppressed. Therefore, the high-accuracy test can be realized without providing, in a separate manner, process and devices for removing noises. As a result, costs for the test can be reduced. Moreover, in order to prevent the interference of noises from the reference electrode 41 and measuring electrode 43, while the intracellular potential is being measured, the well plate 1 may be covered by a net or a box made of metal.

Extracellular potential of the cells contained in wells 3, which is mounted 96-wells in the plate main body 2, can be measured in each wells 3, independently. Therefore, when an amount or kind of drug in each well becomes different, the measurement can be realized by one time under various conditions, and the results can be compared with.

In the above embodiment, the case where the measurement is made by using the reference electrode 41 and measuring electrode 43 is described. However, the state of activity of a cell can be observed by applying an electrical stimulus as added voltage to a cell to be measured from the measuring electrode 43 or an electrode separately prepared. For example, applying an electrical stimulus from the measuring electrode 43 to the cells to be measured and observing the movement of an anionic fluorescent dye having membrane permeability such as bis-oxonol can perform indirect measurement of extracellular potential. This enables to observe the activity state of a cell. Also, by applying specified AC voltages between the reference electrode 41 and measuring electrode 43 and by measuring impedance in the case, activity state of a cell can be observed.

In the above embodiment, the case where the well plate 1 has 96 pieces of wells 3 arranged in a checkered manner on the top plate 2a and opened therein is described. However, the number of the wells 3 mounted in the well-plate 1 and arrangement configuration of the top plate 2a is arbitrary. For example, therefore, 385 or 1536 pieces of the well 3 may be arranged in the checkered manner on the top plate 2a and be opened therein. Furthermore, instead of the well plate 1, a simple tube-shaped configuration can be used.

In the above embodiment, the case where one cell is contained in each well is described. However, the number of cells in each well 3 may be appropriately changed depending on the kind of cells in each well 3 or on an object of the observation.

Also, in the above embodiment, the case is described where the outer dimension of the plate main body 2 can be set according to dimensions of the SBS specifications so that the supply to the cells or the culture media to the well 3 is automatically made. However, in the case where any procedure described above is performed manually without using an apparatus, it is not necessary that the plate main body 2 has the outer dimension designated according to the specification. Moreover, the well plate 1 may have the outer dimension designated according to other specifications, which allow automatic operations by using the apparatus.

The well 3 may be comprised in an arbitrary manner if the measuring electrode 43 has the diameter reduced portion 32 set at a lower end portion. For example, as shown in FIG. 5(a), the internal circumferential surface of the diameter reduced portion 32 may be constructed to have a spherical cone-shape. Also, as shown in FIG. 5(b), the internal circumferential surface of the diameter reduced portion 32 may be constructed so as to be funnel-shaped. Also, as shown in FIGS. 6(c) and (d), the well 3 may be constructed simply of the diameter reduced portion 320 without having the cylindrical portion 31. In the example shown in FIG. 6 (c), the well 3 is constructed of the diameter reduced portion 320, which inner circumferential surface diameter is reduced so as to have a conical shape from the upper end opening to the lower end section. In the example shown in FIG. 6 (d), the well 3 may be constructed of the diameter reduced portion 320, which inner circumferential surface diameter is reduced so as to have a spherical cone-shape from the upper end opening to the lower end portion.

Figure 8:
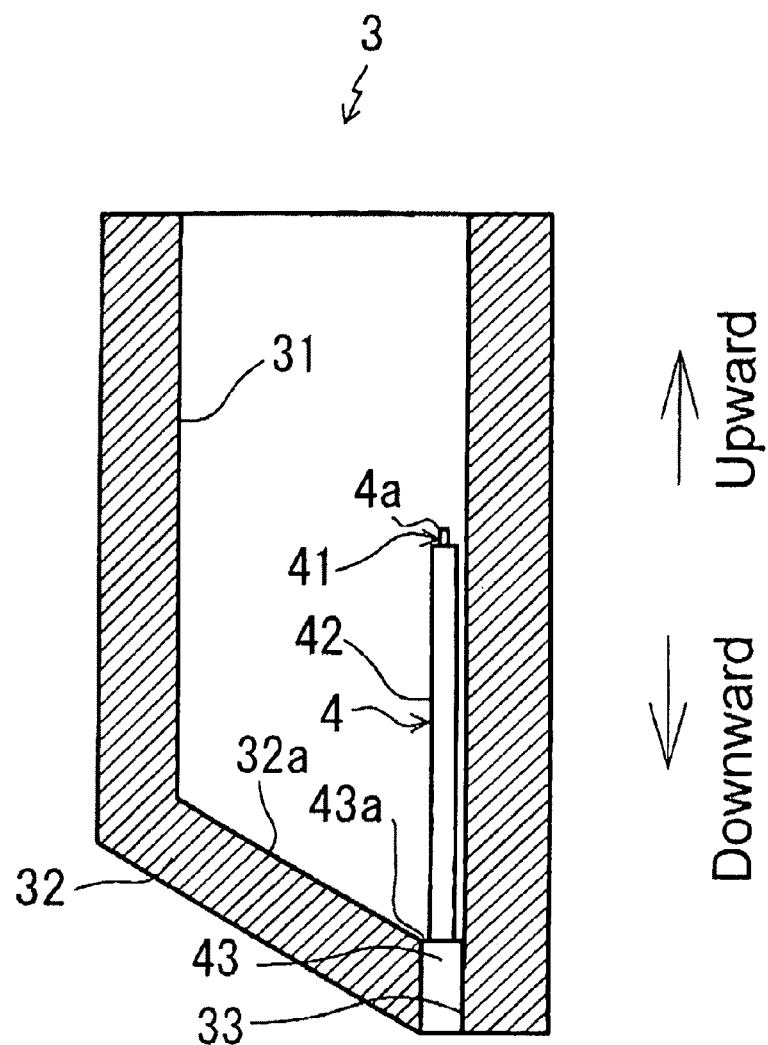
FIG. 8 is a fourth diagram explaining a modified example of a well mounted in the well plate.

Also, as shown in FIGS. 7(e) and 7(f), the well 3 is constructed so that the diameter of an inner circumferential surface of the central section is expanded as compared with the upper and lower end portions. As an example shown in FIG. 7(e), the well 3 has a diameter reduced portion 32, which the diameter of the inner circumferential surface is reduced conically along its central portion to its upper end portion. Also, in an example shown in FIG. 7(f), the well 3 has a spherical inner circumferential surface, which the diameter of its central portion is expanded as compared with its upper and lower end portions. As shown in FIGS. 7(e) and 7(f), the well 3 has an upper opening whose diameter is reduced. Moreover, the lower end portion of the diameter reduced portion 32 which measuring electrode 43 facing the inside portion of the well 3 is not necessarily positioned in a central portion of the inner circumferential surface 32a; and, as shown in FIG. 8(g), it may be positioned in an edge portion of the outer circumferential surface 32a. That is, it is not necessary that the diameter reduced portion 32 has a symmetrical cross section with the lower end portion in which the measuring electrode 43 is disposed being interposed therebetween.

Moreover, the tilted angle of the inner circumferential surface 32a of the diameter reduced portion 32 may be made different stepwise from the upper end side to the lower end side. Also, the plane shape of the well 3 is not only circular but also polygonal and may have an oval or ellipse.

The detecting portion 4 is not limited to the above configuration and is arbitrary if it has a measuring electrode 43 at the lower end portion of the diameter reduced portion 32 contained in the well 3, a reference electrode 41 above the position of the measuring electrode 43, and each facing the inside portion of the well 3. For example, the detecting section 4 may have a bent shape relative to the extending direction of the inserting hole 33, the extending direction is declined relative to a mounted on the inserting hole 33, or the upper end portion 4a of the detecting section 4 abuts or nearly contacts in proximity to the inner circumferential surface of wells 3. Further, the upper end portion 4a of the detecting section 4 being abutted to be in contact with the inner circumferential surface in the well 3 may be fixed to the inner circumferential surface of the well 3.

Also, as the place where the outer circumferential surface of the reference electrode 41 is positioned inside the well 3 is arbitrary if there is a distance between the measuring electrode 43 being enough to allow an ion having moved from the cell on the upper end surface 43a of the measuring electrode 43 to the outside of the cell to be sufficiently diffused. The place is not necessarily positioned in the upper end portion 4a of the detecting section 4. For example, the upper end 4a of the reference electrode 41 may be coated with the insulating section 42, and an outer circumferential surface of the reference electrode 41 positioned under the insulating section 42 may be exposed to the outside. Also, the reference electrode 41 may be exposed only partially or entirely to the outer circumferential surface along the circumferential direction.

Also, it is not necessary that the reference electrode 41 may be constructed integrally with the measuring electrode 43, and the reference electrode 41 and measuring electrode 43 may be configured separately. For example, as shown in FIG. 9 (a), the measuring electrode 43 may be configured to face the inside portion of the well 3 from the direction of the inserting hole 33 and the reference electrode 41 may be configured to face the inside portion of the well 3 from the direction of the through hole 31a formed in the cylindrical portion 31. Also, as shown in FIG. 9(b), the reference electrode 41 can be configured to face the inside portion of the well 3 from the direction of the upper end opening of the well 3. As shown in FIG. 10(a), a groove portion 34 is formed in a circumferential portion of the diameter reduced portion 32 so that the groove portion 34 faces the inside portion of the reference electrode 41. Also, as shown in FIG. 10(b), the reference electrode 41 may be provided in the chamber 37 connecting with the passage 36 mounted on the side wall of the cylindrical portion 31.

Also, as shown in FIG. 11, it can be configured: the plate main body 20 is mounted on a wiring substrate 50 on which the measuring electrode 510 and reference electrode 520 are formed; the measuring electrode 510 is adapted to face the lower end opening 341 of the diameter reduced portion 340 having in the well 30; and the reference electrode 520 is adapted to face the lower end opening of the through hole 350 where the upper end opening is opened at its inner face of the well 3 in a manner being distant from the diameter reduced portion 340.

As shown in FIG. 11(a), a lower face of the plate main body 20 is in close contact with an upper face of the wiring substrate 50, and the well 30 is kept fluid-tight. The well 30 comprises a large diameter cylindrical section 310 extending downward from an upper end opening which opens on an upper face of the plate main body 20, a step difference portion 320 which upper face is extended in parallel to an upper face of the plate main body 20 from a lower end of a large diameter cylindrical section 310, and a small diameter cylindrical section 330 extending downward from the upper end opening being opened at the upper face of the step difference portion.

From the lower end of the small diameter cylindrical portion 330, the diameter reduced portion 340, as described above, extends downward in a cone-shape in which the diameter of the inner circumferential surface is reduced along an upper end side toward its lower end side. As shown in FIG. 11(b), the large diameter cylindrical portion 310, small diameter cylindrical portion 330, and diameter reduced portion 340 are formed as a circular plane shape with respective axis being matched. Also, in the diameter reduced portion 340, a tip portion of the measuring electrode 510 is adapted to face the inside portion of the well 30 from the direction of the lower end opening 341 being opened on a lower end of the plate main body 20. The inner diameter of the lower end opening 341 is set to be large enough to make a cell to be used in the measurement by the well plate 1 be in contact with a tip of the measuring electrode 510.

As shown in FIGS. 11(a) and 11(b), the through hole 350 as described above is opened at the step difference portion 320 with an interval between the through hole 350 and the upper end opening of the small cylindrical portion 330. The through hole 350 extends along an inner circumferential surface of the large diameter cylindrical portion 310. The large diameter cylindrical portion 310 extends within a predetermined angle range centering on an axis (270 degrees in the example) of the large diameter cylindrical portion 310 and have a plane shape in which an annular body is partially notched.

As shown in FIG. 11(c), the reference electrode 520 has a plane shape in which an annular body is partially notched and extends along the through hole 350 of the well 30 and is adapted to face the lower end opening of the through hole 350. The measuring electrode 510 enters from the outside through a cutout potion of the reference electrode 520 into its inner side so that a tip positioned in the central portion of the reference electrode 520 is adapted to face the lower end opening 341.

When a drug test is made based on extracellular potential of a cell by using the well plate 1 having the configurations described above, cells to be inspected are applied one by one into the small cylindrical portion 330 of each well 30 from the upper end opening. The cells put into a cell culture move downward, by self weight, through the diameter reduced portion 340 and adhere to the tip of the measuring electrode 510 through the lower end opening 341.

Thereafter, when the culture medium is supplied into the through hole 350 via the small diameter cylindrical portion 330 so that the through hole 350 is filled with the culture medium and when the culture medium is supplied to the well 30 to the extent to which the step difference portion 320 is covered by the liquid surface, and the reference electrode 520 is connected to the measuring electrode 510 by the culture medium to enable the extracellular measurement of cells in a small cylindrical portion 30.

According to the configuration, the small cylindrical portion 330 providing the diameter reduced portion 340 is separated by the step difference portion 330 from the through hole 350; and, therefore, by introducing the culture medium containing cells into the small diameter cylindrical portion 330, the adherence of cells in the culture medium to the reference electrode 520 can be prevented. Thereby, it simplifies the work of applying cells.

Also, the measuring electrode 510 and reference electrode 520 can be formed on the wiring substrate 50 with wiring and/or circuit to be used for connection with external devices. Therefore, it is possible to simplify the configuration of a detecting section comprised the measuring electrode 510 and reference electrode 520.

In addition, the arranging shape of measuring electrode 510 on the wiring substrate 50 and the shape of the diameter reduced portion 340 and the lower end opening 341 can be formed as an arbitrary shape so as cells are in contact with the measuring electrode 510 facing the lower end opening 341.

Moreover, the arranging shape of reference electrode 520 on the wiring substrate 50 is as an arbitrary manner so as the reference electrode 520 can face the lower end opening of trough hole 350.

Also, the through hole 350 may be formed in an arbitrary manner so as the through hole 350 is separated from the small diameter cylindrical portion 330 and is allowed to pass through a lower face of the plate main body 20 and the reference electrode 520 can face the lower end opening. Moreover, it is not necessary that the large diameter portion, small diameter portion, and diameter reduced portion have the circular and plane shape and are formed coaxially.

In the above embodiment, the case is described in which the culture medium is supplied to the well 3 until the entire surface of the outer circumferential surface 32a of the diameter reduced portion 32 is covered by the liquid surface.

However, as shown in FIGS. 6(c) and 6(d), when the well 3 has only the diameter reduced portion 320, or, as shown in FIGS. 7(e) and 7(f), when the inner circumferential surface of the central portion of the well 3 is expanded more compared with the upper end portion and lower end portion, it is not necessary that the entire surface of the diameter reduced portions 32 and 320 are covered with the culture medium.

Also, in the above embodiment, the case is described in which the culture medium is additionally supplied after the adhesion of cells applied into the well 3. However, the culture medium can be additionally supplied without waiting the adhesion of cells. Also, the centrifugal force may be applied by using an apparatus such as a centrifuge either for a period between the applying cells to the well 3 and the staying of cells on the upper end surface 43a of the measuring electrode 43, or for a period before the adhesion of cells 3 to the upper end surface 43a.

Also, any material may be used as a material for the Well plate 2, insulating portion 42 having in insulating section 4, and the wiring substrate 5. For example, polypropylene can be used. Also, by performing hydrophobic coating, by using fluorine or Teflon (Trade Mark) on the inner surface of the well 3 or on the surface of the insulating section 42, the adhesion of cells can be prevented. This enables the tilt angle of the inner circumferential surface 32a of the diameter reduced portion 32 to be decreased, and applying cells can be leaded to the upper end portion 43a of the measuring electrode 43. Also, when a material apprehensible to the adhesion of cells is used as a material for the insulating portion of the well 3 or detecting section 4, the adhesion of cells can be prevented. Further, by performing hydrophilic coating, by using collagen, gelatin, polylysine, or the like, on the upper end surface 43 of the measuring electrode 43, cells are promoted to the adhesion on the upper end surface 43a.

EXAMPLE

By using an example, a cell measuring container of the embodiment of the present invention is explained more specifically. The example is one example of the embodiment and the present invention is not limited to the example.

At first, as refer to FIG. 12, there is provided an example of the measurements of a potential of a cardiac muscle cell (hereinafter, referred to as a pulsating cell), as a cell to be measured which pulsates, by using the first embodiment of the present invention as shown in FIG. 11.

(Potential Measurements of Pulsating Cell Immediately after Contact)

The pulsating cell was obtained by performing a process of differentiation of a cardiac muscle cell from an ES (Embryonic Stem) cell to obtain a colony of the pulsating cell. Then, a pulsating single cell, a plurality of cells, or a cell mass was extracted and prepared by putting the colony on a pointed end of a micropipette tip or by using a device such as a cell colony picker.

Subsequently, the obtained pulsating cell was applied with a liquid medium to the well having a cone-shaped structure of the embodiment of the present invention. The pulsating cell is precipitated by self-weight to the measuring electrode. As the liquid medium for pulsating cell, a publicly known DMEM (Dulbecco's Modified Eagle's Medium) was used.

Then, cells applied with a liquid medium are cultured at 37° C., 5% $CO_2$, and 100% humidity.

Then, after culturing the pulsation cells, by adding a under-test compound having a pre-determined concentration in respective experiments described below, the measurements of a potential were performed. The concentration of under-test compound is adjusted by dissolving the compound in a known medium containing DMSO (Dimethyl sulfoxide,) etc., or by directly dissolving the compound in measuring liquid, such as a culture medium for measurements. Then, at the time of measurements, the extracellular liquid is replaced with an appropriate culture medium for measurements or a buffer for measurements.

Figure 12:
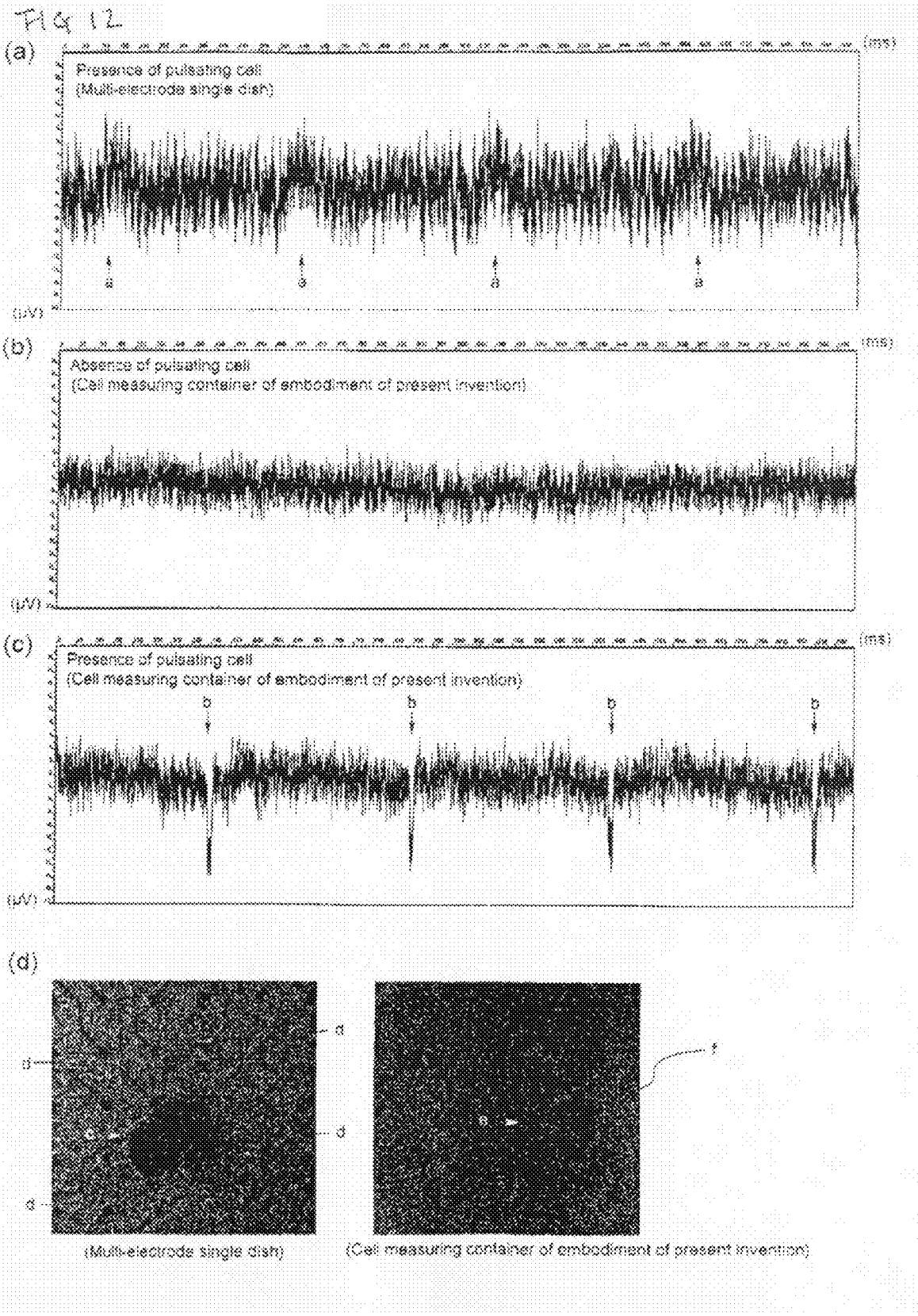
FIG. 12 is a photograph showing an example of the measurement of extracellular potential of a cell.

Then, by referring to FIG. 12, an example in which extracellular potentials of cells are compared is described. The vertical axis shows measuring potential (μV), and horizontal axis indicates measuring time (ms).

FIG. 12(a) shows an example of the extracellular potential obtained by measuring a pulsation cell and by using an MEA (multi-electrode array) system, which is a conventional multi-electrode single dish type extracellular potential measurement system. This multi-electrode single dish is formed a plurality of electrodes, which is highly concentrated and accumulated at a center of the dish, and, when cells become in touch with the measuring electrode in the dish, extracellular potential is recorded (As refer to: Bioresearch Center, MEA system, [online], retrieved on Sep. 10, 2008, Internet <URL: http://www.brck.co.jp/MCS/meacataloguejpl.pdf>). In the measurement of a potential of the multi-electrode single dish shown in FIG. 12 (a), a colony is put on the electrode by using a pipette. The pipette is taken out with the greatest care, and it is confirmed that the colony is placed on the electrode. Then, the measurement is carried out. The colony of the pulsation cell measured in FIG. 12(a) was attached a plurality of the electrodes, and the pulsation of cells was also confirmed visually.

FIG. 12 (b) is a control example, which shows potentials measured without applying any cell by using the cell measuring container according to the embodiment of the present invention.

FIG. 12 (c) shows an example of an extracellular potential measured by using the cell measuring container according to the embodiment of the present invention, in which pulsation cells are actually applied. In the measurement of a potential by the cell measuring container, immediately after cells were added, the pipette was pulled out. Then, after waiting the cells were naturally precipitated on the bottom of the electrode of the cell measuring container, or after cells being precipitated by small centrifugal force, the measurement was performed. In FIG. 12(c), the measured pulsation cell colony was in contact with the measuring electrode, and the pulsation of cells was visually confirmed.

The left photo in FIG. 12(d) shows the pulsation cell colony "c" placed in the multi-single dish shown in FIG. 12(a), and the right photo in FIG. 12(d) shows the pulsation cell colony "e" placed in the cell measuring container shown in FIG. 12(c) of the embodiment of the present invention. Both in the case of the multi-electrode single dish and in the case of the cell measuring container, the measurement can be done when a pulsation cell colony is in contact with one or more electrodes "d" or measuring electrode "f".

Each potential shown in FIGS. 12(a), (b), and (c) is measured by connecting an electrode terminal of the cell measuring container to a connecting terminal of the measuring device of the above QT screen type. Then, data is analyzed by using attached software on the above QT screen.

In FIG. 12(a), in the extracellular potential measured by the conventional multi-electrode MEA system containing pulsation cells, the waveform peaks "a", which are considered to be a signal from the pulsation cell, were confirmed at approximately 100, 600, 1100, 1600 ms.

The well containing no pulsation cell as shown in FIG. 12 (b) is a control case, and, therefore, no potential peak was detected.

In the case of the well containing pulsation cells shown in FIG. 12(c), after cells were applied, the waveform peak "b" was measured at 400, 900, 1400, 1900 ms. When compared with the case by using the conventional MEA system in FIG. 12(a), the appearance interval itself of the pulsation was about 500 ms in the same manner as above, and the waveform peak "b" having a high visibility with sharp shape was detected.

The followings have been found from these experiment results.

Firstly, in the conventional electrode mounted at a plane bottom of the culture container of the QT screen type, it was very difficult to place cells at a center of the electrode. Therefore, actually, the measurement of the extracellular potential was impossible.

Unlike the conventional case, by using the cell measuring container according to the embodiment of the present invention having a cone-shaped structure, the pulsation cell is in contact with the measuring electrode. This enables a waveform having a sharp peak from the electrode is to be confirmed.

Also, in the multi-electrode single dish by using the conventional MEA system, cells are simply put on the dish for culture. Therefore, cells are applied on the dish with the greatest care. Another problem is that, when cells are put into the dish by using a colony picker, if the cell adding section of the colony picker is pulled out immediately after the supply of the cell, a culture medium is disturbed causing the cell being peeled off from the electrodes. Thus, when the colony picker is used, after confirming by using a microscope that cells are in contact with the measuring electrode on the dish. Then, it is need to wait at least 6 hours, and the cell adding section is pulled out.

Unlike the conventional case, when the measurement is performed by using the cell measuring container of the embodiment of the present invention, cells are naturally precipitated immediately after applying the cell, and the cells contact with electrode without requiring a positioning process, etc. Therefore, the effect can be obtained that the application of cells with ordinary micropipette, etc., without requiring much care, and the measurement can be started immediately. In addition, immediate start of the measurement is possible even in the case where the colony picker is used. It was found that the pulsation waveform at the same level could be detected because the waveform, interval, and amplitude being the same waveform as in the case of the conventional multi-electrode single dish of the MEA system were contained in the obtained waveform. Further, in the well containing no pulsation cell, no waveform could be detected. Therefore, it was confirmed that the measurement by using the cell measuring container of the embodiment of the present invention is not interfered by noises or the like. Thus, the extracellular potential of the pulsation cell could be surely measured by using the cell measuring container of the embodiment of the present invention.

As just described, in the waveform of the extracellular potential obtained by using the cell measuring container of the embodiment of the present invention, appearance of a clear peak waveform was achieved. That is, by using the potential measuring method of the embodiment of the present invention, it was found that, even in the case of the ES cell derived cardiac pulsation cell or the like in which the obtaining of the sufficient number of cells was impossible, a clear peak waveform having the same level as in the multi-electrode single dish of the conventional MEA system was easily obtained to measure extracellular potential.

Moreover, in the examples, in order to achieve reproducibility, an experiment was made on another cardiac muscle cell having different number of pulsations by using the same well, and similar evaluation results were obtained. Moreover, peak detection frequency or period changes in every different pulsation cell in addition to have different waveform in every different pulsation. Therefore, there was low possibility that a noise was peculiar to the well.

(Measurement of Extracellular Cell Potential after the Adhesion of Pulsation Cell)

Then, as refer to FIG. 13, the measurement of extracellular potential after adhesion of a pulsation cell on the measuring electrode is explained.

FIG. 13(a) shows an extracellular potential obtained by the measurement of the pulsation cell adhered on the measuring electrode of the cell measuring container of the embodiment of the present invention by culturing for one day. The vertical axis shows a measuring potential ($\mu$V), and horizontal axis shows a measuring time (ms). It was confirmed that the waveform contained a sharp peak "g" approximately at 700 ms, and the waveform contained a slow rise "h" approximately at 1100 ms. Moreover, the sharp waveform peak "g" shows a $Na^+$ current peak indicating the opening and closing of the $Na^+$ channel and the waveform "h" showing a slow rise is the $K^+$ current peak indicating the opening and closing of $K^+$ channel (Anal Bioanal Chem. 2003 October; 377(3): 486-495, Review). Moreover, it is characterized that the sharp waveform peak "g" is similar to a QRS-like waveform in an electrocardiogram, and the waveform "h" showing the slow rise is similar to a T-wave like waveform.

FIG. 13 (b) shows a photograph confirming a position of the pulsation cell under a stereoscopic microscope. The pulsation cell colony "i" was in contact with a measuring electrode "f" in the central, and pulsation of the cell was visually confirmed. Moreover, the vibration of the plate caused no change in the position of the pulsation cell.

The following conclusions have been found by the above experiment.

Firstly, even when cells were cultured for a long time by using the cell measuring container of the embodiment of the present invention, the measurement of outer potential of a cell can be performed. Thus, it was found by using the cell measuring container of the embodiment of the present invention, even when a drug was supplied to a pulsation cell a plurality of times, and a measurement can be possible even after cells were re-cultured.

Further, when a cell membrane is measured by using a conventional patch clamping method, the cell is destroyed, and, therefore, the measurement is impossible by using the cell which has been once used for the measurement. On the other hand, in the case of the multi-electrode single dish by using the conventional MEA system, an extracellular potential was measured, and, therefore, the cell could be reused theoretically. However, the cells had to be taken out while being checked by an operator by a microscope, which took much time and labor, and the re-use of the cells was not practical.

Unlike the above method, in the case of the cell measuring container of the embodiment of the present invention, the bottom of the container has a cone shape. Thus, the cells having been naturally precipitated ensured to adhere on the electrode. This enables the cell can be taken out from the bottom of the container by using a pipette and re-cultures. Thus, the effect of easily reusing the cell is obtained. Also, because the position of the bottom of the cell measuring container can be determined with high accuracy, it enables the cell to be pulled out by using a device easily.

Moreover, in the conventional MEA system, it is necessary to provide a plurality of electrodes to one culture container. Therefore, to form an electrode on a plate having a plurality of wells such as a 96-well plate or the like, a pattern of the electrode had to be prepared for each well. Due to this, costs are too high which makes it difficult to fabricate the multi-electrode type cell measuring container having a plurality of wells. Unlike the above case, by using the cell measuring container of the embodiment of the present invention, even if the number of measuring electrodes is only one, contact of cells to be measured with the electrode easily is made possible. As a result, the extracellular potential measuring method can be provided at low costs. Therefore, by using the 96-well plate or the like of the embodiment of the present invention, the drug evaluation system for the prolongation of the QT interval can be constructed, and drug discovery screening having high throughput was made possible. Furthermore, by using a structure in which the wiring substrate and the plate main body are fabricated separately and are patched together, a low cost cell measuring container can be produced.

EXPLANATION OF NUMERALS AND CHARACTERS

1: Well plate, 2, 20: Plate main body, 3, 30: Well, 31: Cylindrical portion, 32: Diameter reduced portion, 32a: Inner circumferential surface, 33: Inserting hole, 310: Large diameter cylindrical section, 320: Step difference portion, 330: Small diameter cylindrical section, 340: Diameter reduced potion, 341: Lower end opening, 350: Through hole, 4: Detecting section, 4a: Upper end portion, 4b: Lower end portion, 4c: Diameter expanded portion, 41: Reference electrode, 42: Insulating portion, 43: Measuring electrode, 5: Wiring substrate, 5a: Through hole, 50: Wiring substrate, 51: Upper face connecting terminal, 52: Lower face connecting terminal, 510: Measuring electrode, 520: Reference electrode, a: Waveform peak (multi-electrode single), b: Waveform peak (cell measuring container of embodiment of the present invention), c: Pulsation cell colony (multi-electrode single dish), d: electrode (multi-electrode single dish), e: Pulsation cell colony (cell measuring container of embodiment of the present invention), f: Measuring electrode (cell measuring container of embodiment of the present invention), g: Sharp waveform peak, h: Waveform showing slow rise, i: Pulsation cell colony.

What is claimed is:

1. A cell measuring container comprising:
   at least one housing chamber being opened at its upper face; and
   a wiring substrate having a measuring electrode, a reference electrode, and the at least one housing chamber; wherein
   the at least one housing chamber has a large diameter portion extending downward from an upper end opening and a small diameter portion extending downward from the large diameter portion through a step difference; and
   the small diameter portion has a diameter reduced portion which diameter of an inner face is reduced from an upper end side to a lower end side and which lower end opening is faced by the measuring electrode, and on an upper face of the step difference portion is mounted an upper opening of a through hole extending apart from the small diameter portion and the lower end opening of the through hole is faced by the reference electrode, wherein the through hole extends along an inner circumferential surface of the large diameter portion.

2. An extracellular potential measuring method for measuring the extracellular potential of a cell comprising the steps of:

using the cell measuring container of claim 1, supplying a culture medium to the at least one housing chamber until an inner circumferential surface of the diameter reduced portion is covered by the culture medium;

supplying a cell to be measured into the culture medium, placing the cell on the measuring electrode, and adhering the cell to the measuring electrode;

supplying the culture medium to the at least one housing chamber until the reference electrode is soaked either before the cell supplying step, after the cell placing step, or after the adhesion of the cell to the measuring electrode; and measuring an extracellular potential of the cell adhered to the measuring electrode based on a potential difference between the reference electrode soaked in the culture medium and the measuring electrode.

3. The method of claim 2, further comprising measuring an extracellular potential of the cell before and after supplying a drug to be inspected into the at least one housing chamber to inspect an influence of the drug on the cell.

4. A cell measuring container comprising:

at least one housing chamber being opened at its upper face and containing a cell with a culture medium, wherein the at least one housing chamber includes: a large diameter portion extending downward from the open upper face and a small diameter portion extending downward from the large diameter portion through a step difference; and the small diameter portion has a diameter reduced portion which diameter of an inner circumferential surface is reduced from an upper end side toward a lower end side;

a measuring electrode placed in the lower end side of the diameter reduced portion; and a reference electrode placed in a position apart from the measuring electrode so as to avoid contact with a cell; wherein the measuring electrode and the reference electrode are formed on a wiring substrate having the at least one housing chamber, the diameter reduced portion faces the measuring electrode on an opening of the lower end, and a through hole extends along an inner circumferential surface of the large diameter portion, apart from the small diameter portion and a lower end opening of the through hole is faced by the reference electrode.

5. An extracellular potential measuring method for measuring the extracellular potential of a cell comprising the steps of:

using the cell measuring container of claim 4, supplying a culture medium to the at least one housing chamber until an inner circumferential surface of the diameter reduced portion is covered by the culture medium;

supplying a cell to be measured into the culture medium, placing the cell on the measuring electrode, and adhering the cell to the measuring electrode;

supplying the culture medium to the at least one housing chamber until the reference electrode is soaked either before the cell supplying step, after the cell placing step, or after the adhesion of the cell to the measuring electrode; and measuring an extracellular potential of the cell adhered to the measuring electrode based on a potential difference between the reference electrode soaked in the culture medium and the measuring electrode.

6. The method of claim 5, further comprising measuring an extracellular potential of the cell before and after supplying of a drug to be inspected into the at least one housing chamber to inspect an influence of the drug on the cell.

* * * * *